United States Patent [19]

Takeda

[11] Patent Number: 4,646,728

[45] Date of Patent: Mar. 3, 1987

[54] DEVICE FOR RELAXING THE SKIN OF THE HEAD

[76] Inventor: Iichiro Takeda, 6-15-33, Ohizumigakuencho, Nerima-ku, Tokyo, Japan

[21] Appl. No.: 729,207

[22] Filed: May 1, 1985

[30] Foreign Application Priority Data

May 19, 1984 [JP] Japan .................. 59-101412

[51] Int. Cl.$^4$ ............................................. A61F 5/24
[52] U.S. Cl. .................... 128/97; 128/76 R; 2/171.2
[58] Field of Search ............... 128/1 R, 97, 76 R, 163, 128/169, 327; 2/171.2, DIG. 11, 171, 185 R

[56] References Cited

U.S. PATENT DOCUMENTS 4,210,147  7/1980  Nestor et al. ............... 128/327
4,248,215  2/1981  Bleakley ........................ 128/97

FOREIGN PATENT DOCUMENTS 698214  11/1930  France ............................ 2/171

Primary Examiner—Carroll B. Dority, Jr.
Attorney, Agent, or Firm—Holman & Stern

[57] ABSTRACT

The skin of the head is pushed up with head skin push-up means to forcibly produce wrinkles in the skin of the top of the head and the forehead and thereby relax the head skin of these portions.

11 Claims, 16 Drawing Figures

DEVICE FOR RELAXING THE SKIN OF THE HEAD

BACKGROUND OF THE INVENTION

1. Field of the Invention

This invention relates to a device for relaxing the skin of the head, which can forcibly generate wrinkles in the skin of the head, particularly the top of the head and the forehead, to thereby relax the skin of the head to prevent depilation and promote growth of hair.

2. Prior Art

Heretofore, there has been proposed no device for relaxing the sink of the head.

SUMMARY OF THE INVENTION

The tension in the skin of the head is thought to be a cause of the depilation of male type (or socalled premature baldness). The skin of the head is present between venter frontalis and venter occipitalis. If the skin of the head is stretched too taut, it will cause troubles in the circulation of blood and lymph. This in turn will cause hair nutrition lesion to cause the depilation.

In view of the fact that the tension in the skin of the head is a cause of the depilation of the male type as noted above, the inventor has thought that it would be possible to prevent depilation and promote hair growth by forcibly producing wrinkles in the skin of the head by pushing up the skin, particularly of the top of the head and the forehead, thereby relaxing the skin of the head, and has completed the invention after extensive experiments.

An object of the invention, accordingly, is to relax the skin of the head, particularly the top of the head and the forehead.

Another object of the invention is to relax the skin of the head by forcibly producing wrinkles in the skin of the head, particularly the top of the head and forehead, by pushing up the head skin.

A further object of the invention is to relax the skin of the head by forcibly producing wrinkles in the skin of the head, particularly the top of the head and the forehead, by pushing up the head skin with head skin push-up means, therely preventing depilation and promoting hair growth.

DETAILED DESCRIPTION OF THE PREFERRED EMBODIMENT

Figure 1:
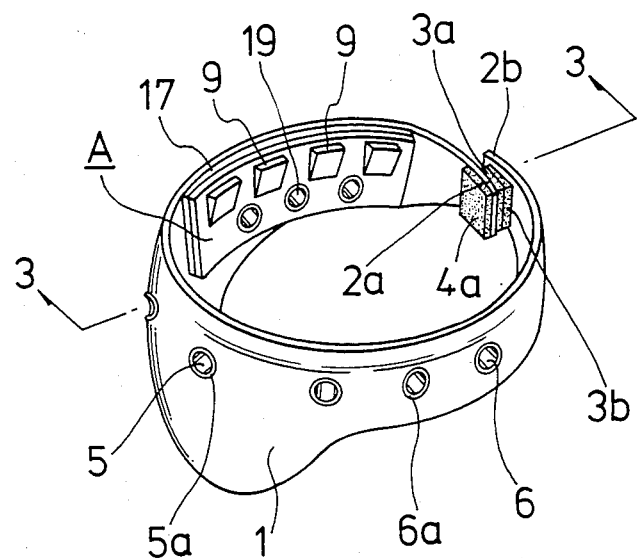
FIG. 1 is a perspective view showing a device for relaxing the skin of the head according to the invention.
Figure 2:
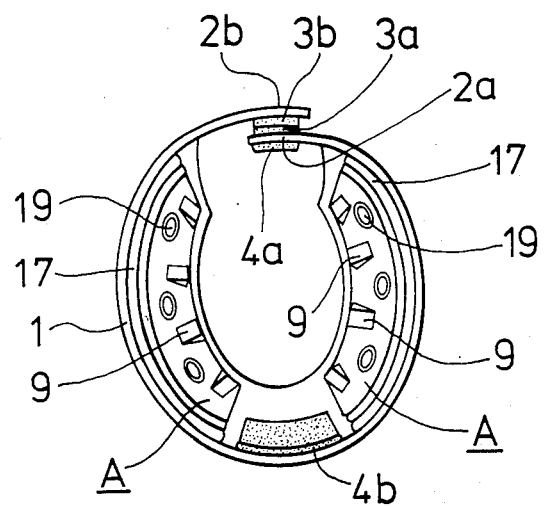
FIG. 2 is a bottom view of the device shown in FIG. 1.

Referring to FIGS. 1 and 2, there is shown a topless attachment member 1 which is to be attached to the head. The illustrated shape of the attachment member is not limitative, but the attachment member may have any shape so long as it can be attached to the head. The opposite ends 2a and 2b of the attachment member 1 are fastened together on the front of the head when it is worn. To this end, the ends 2a and 2b of the member are provided with respective male and female fasteners 3a and 3b (which are available under a trademark "Magic Fastener") such that the fasteners 3a and 3b are attached to each other with the respective ends overlapped over each other when the attachment member 1 is worn. The attachment member 1 further has soft cushioning members 4a and 4b provided on front and rear portions of its inner side. When the attachment member 1 is worn on the head, the cusioning members 4a and 4b are in contact with the head and provide a buffering action to protect the head. The attachment member 1 further has a plurality of air passage holes 5 formed on a rear portion and a plurality of air passage holes 6 formed on each side portion to prevent its inside from getting musty when it is worn. In this embodiment, ring-like members 5a and 6a are provided at the holes 5 and 6 to prevent breakage of the member 1 from these holes 5 and 6. The ring-like members 5a and 6a can be dispensed with.

On each inner side of the attachment member 1 having the above structure is provided a head skin push-up member A. The head skin push-up members A serve to push up the sides of the head, particularly the top of the head and forehead, to forcibly produce wrinkles and thereby relax the head skin.

Figure 3:
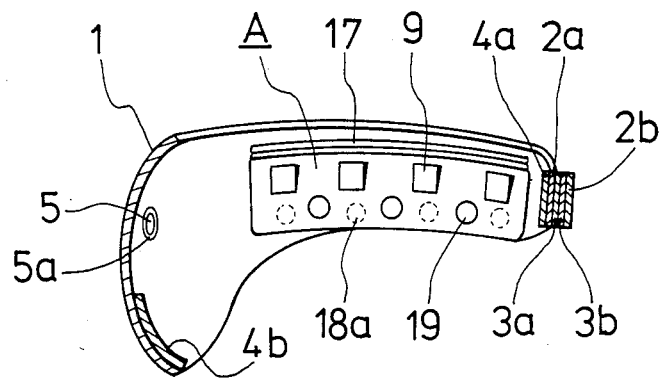
FIG. 3 is a sectional view taken along line 3—3 in FIG. 1.
Figure 4:
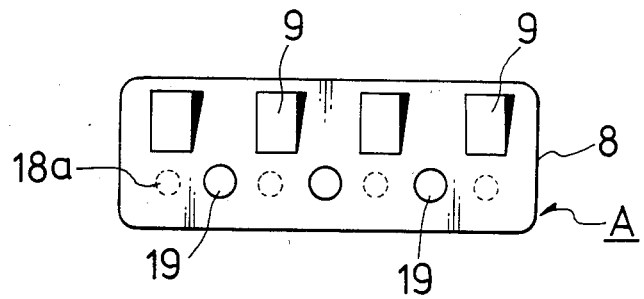
FIG. 4 is a front view showing a first example of head skin push-up member.

FIG. 3 is a sectional side view taken along line 3—3 of FIG. 1, and air passages 19 which are also seen in FIG. 1. FIG. 4 also shows the air passages 19, as part of the head skin push-up member A.

Figures 5, 6:
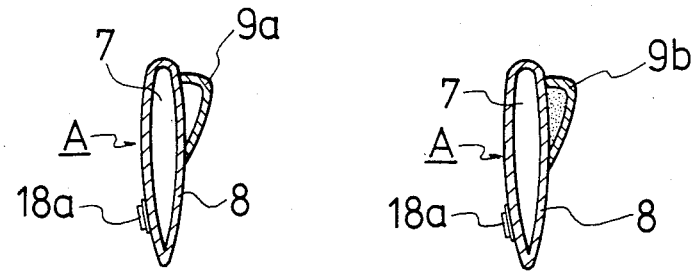
FIG. 5 is a transversal sectional view showing the head skin push-up member shown in FIG. 4.
FIG. 6 is a view similar to FIG. 5 but showing a modification of the head skin push-up member shown in FIG. 5.

The head skin push-up member A may have any structure so long as it has protuberances effective to push up the head skin. FIGS. 4 through 8 illustrate some examples of the head skin push-up member A. In the arrangement shown in FIGS. 4 to 6, the member A comprises an elongate hollow member 8 made of a soft material such as latex and soft plastics and having an air chamber 7, in which a predetermined quantity of air is sealed in advance. A plurality of substantially triangular protuberances 9 are provided at a predetermined interval on the inner side of the elongate hollow member 8. The protuberance 9 may be a hollow member 9a as shown in FIG. 5, or it may be filled with a cushioning member or the like and constitute a solid member 9b as shown in FIG. 6.

Figure 7:
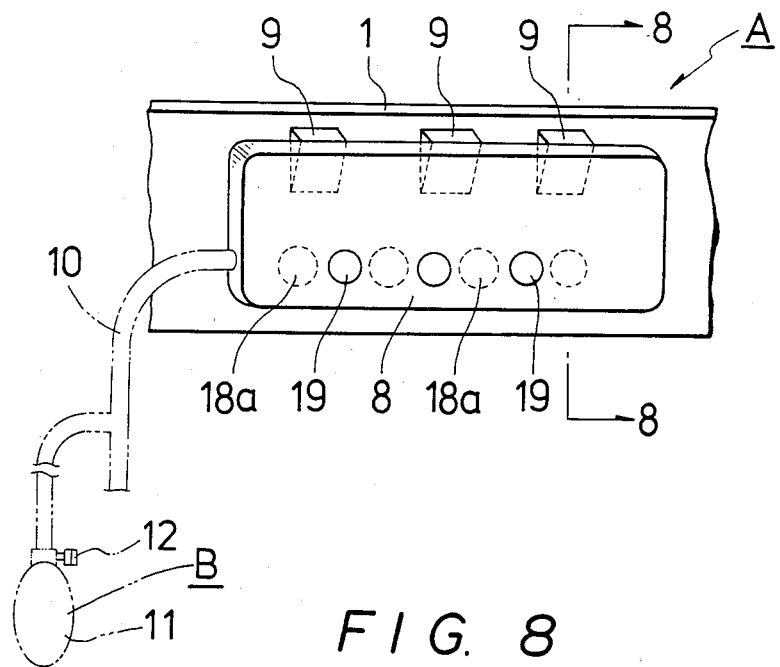
FIG. 7 is a perspective view showing a modification of the first example of the head skin push-up member.
Figure 8:
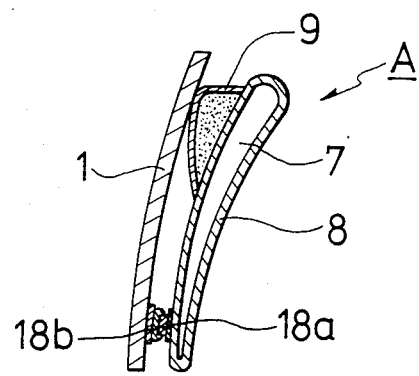
FIG. 8 is a sectional view taken along line 8—8 in FIG. 7.

FIGS. 7 and 8 show a modification of the example of FIGS. 4 to 6. This arrangement comprises an elongate hollow member 8 made of a soft material such as latex and soft plactics and having an air chamber 7 and a plurality of triangular protuberances 9 provided at a predetermined interval on the outer side of the elongate hollow member 8. In this instance, a required amount of air is supplied into the air chamber 7 by air supplying means B whenever the attachment is worn on the head. In the illustrated example, the air supplying means B includes an air supply tube 10 connected to the air chamber 7 and an air supply ball 11 provided at the other end of the air supply tube 10. A necessary amount of air for pushing up the skin of the head is supplied into the air chamber 7 through the air supply tube 10 by pushing the air supply ball 11. Subsequently, an on-off valve 12 is closed to maintain the skin of the head in the pushed-up state. As air is supplied into the air chamber 7, each protuberance 9 is first brought into contact with the attachment member 1, and the degree of contact is progressively increased. Eventually, an inward pushing force is given to a portion of the elongate hollow member 8 corresponding to the protuberance 9, thus pushing up the skin of the head. The protuberance 9 may be either hollow or solid.

Figure 9:
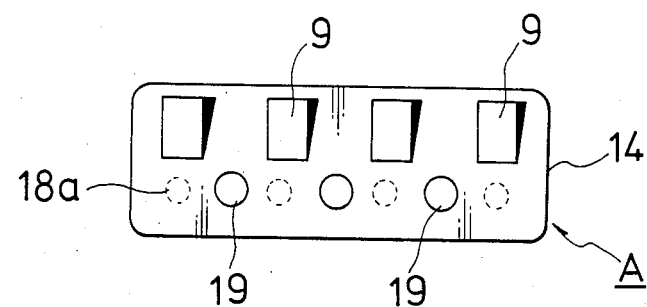
FIG. 9 is a front view showing a second example of the head skin push-up member.
Figure 10:
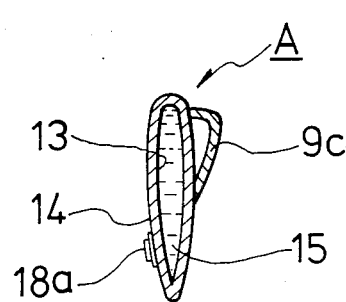
FIG. 10 is a sectional view showing the head skin push-up member shown in FIG. 9.
Figure 11:
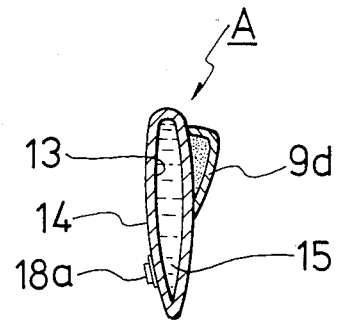
FIG. 11 is a view similar to FIG. 10 but showing a modification of the head skin push-up member shown in FIG. 10.

FIGS. 9 to 11 show a different modification of the head skin push-up member A. This arrangement comprises an elongate hollow member 14 made of a soft material such as latex or soft plastic materials and having a chamber 13, which is filled with a fluid 15, e.g., a gas or water, and a plurality of protuberances 9 provided at a predetermined interval on the inner side of the elongate hollow member 14. Each protuberance 9 may be a hollow member 9c as shown in FIG. 10, or it may be filled with a cushioning member to constitute a solid member 9d as shown in FIG. 11.

Figure 12:
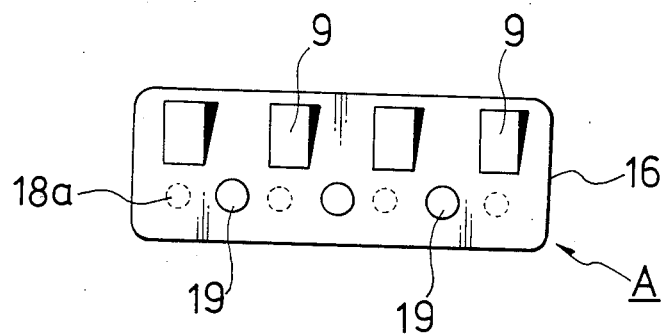
FIG. 12 is a front view showing a third example of the head skin push-up member.
Figure 13:
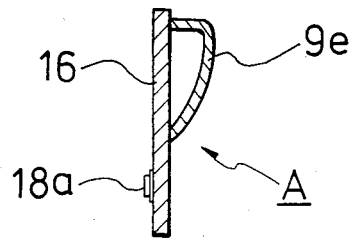
FIG. 13 is a sectional view showing the head skin push-up member shown in FIG. 12.
Figure 14:
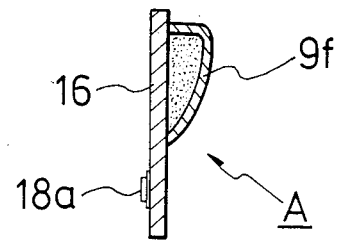
FIG. 14 is a view similar to FIG. 13 but showing a modification of the head skin push-up member shown in FIG. 13.

FIGS. 12 to 14 show a further modification of the head skin push-up means A. This arrangement comprises an elongate member 16, which is a thin plate of rubber or the like, and a plurality of protuberances 9 provided at a predetermined interval on the innder side of the elongate member 16. Each protuberance 9 may be a hollow member 9e as shown in FIG. 13, or it may be filled with a cushioning material to constitute a solid member 9f as shown in FIG. 14.

The head skin push-up member A as described above is detachably mounted on the attachment member 1. It is mounted in different ways when the attachment member 1 is made of a soft material and when the attachment member 1 is made of a hard material.

Figure 15:
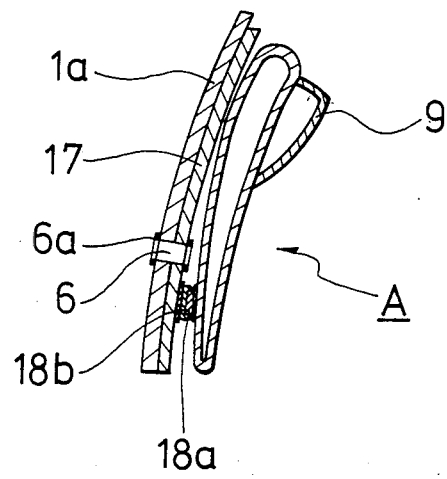
FIG. 15 is a sectional view showing means of installing head skin push-up member on attachment member made of a soft material.

In case when the attachment member 1 is made of a soft material 1a such as soft plastics as shown in FIG. 15, a shape retaining member 17 consisting of a thin plate of a hard material is secured to each inner side of the attachment member 1a (the shape retaining member 17 being also shown mounted in FIGS. 1 to 3) to prevent deformation of the attachment member 1a. The shape retaining member 17 is secured to the attachment member A by the ring-like members 6a provided at the air passage holes 6 noted above. The head skin push-up member A may be installed on the attachment member 1a by any suitable means. Preferably, the two may be coupled together with male and female hook members 18a and 18b respectively secured to the head skin push-up member A and shape retaining member 17. In the first to third examples shown in FIGS. 4 to 14, make hook member 18a is shown as means for securing the head skin push-up member A to the attachment member 1.

Figure 16:
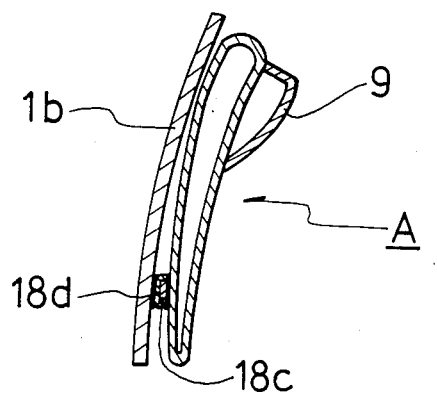
FIG. 16 is a sectional view showing means of installing head skin push-up member on attachment member made of a hard material.

In case when the attachment member 1 is made of a hard material 1b such as hard plastics, there is no possibility of deformation of the attachment member 1b. Therefore, the shape retaining member 17 used for the attachment member 1a shown in FIG. 15 is unnecessary. Again in this case, the head skin push-up member 1b may be secured to the attachment member A by any suitable means. Preferably, the two may be coupled together with male and female hook members 18c and 18d respectively secured to the head skin push-up member A and attachment member 1b as shown in FIG. 16.

It is recommendable that the head skin push-up member A is provided with air passage holes 19 at positions coinciding with the air passage holes 6 of the attachment member 1 to prevent the inside of the attachment member 1 from becoming musty when the attachment member 1 is worn.

The function of the device for relaxing the head skin described above according to the invention will now be explained. When the attachment member 1 is worn on and attached to the head by attaching together the male and female fasteners 3a and 3b at its opposite ends such that it is securely held in position by the forehead and the back of the head, the substantially triangular protuberances 9 of the head skin push-up members A are deformed to fit the shape of the head. Consequently, a force is exerted to the head such that it tends to push up the skin of the head to forcibly generate wrinkles in the head skin in the top of the head and forehead. The extent of generation of wrinkles can be suitably adjusted by adjusting the position of fastening of the attachment member 1 with the fasteners 3a and 3b. The attachment member 1 is suitably worn for 2 hours a day.

As has been described in the foregoing, with according to the invention by merely wearing the attachment member 1 on the head the skin of the head is pushed up by the head skin push-up members A to forcibly generate wrinkles in the top of the head and forehard and thus relax the head skin in these portions, which is effective for preventing depilation the promoting hair growth. Further, it is possible to replace the head skin push-up member A with replacing means.

What is claimed is:

1. A device for relaxing the skin of the head, comprising an attachment member capable of being removably attached to the head, and head skin push-up members each provided on each inner side of said attachment member; said head skin push-up members each including an elongate member made of a soft material and having an air chamber filled with a predetermined amount of air and a plurality of protuberances provided at a predetermined interval on the inner side of the said elongate member.

2. The device for relaxing the skin of the head according to claim 1, wherein said head skin push-up members are capable of being removably installed on said attachment member.

3. The device for relaxing the skin of the head according to claim 1, further comprising an air supplying means, air being supplied when desired into said air chamber with said air supplying means.

4. The device for relaxing the skin of the head according to claim 1, wherein said protuberances are hollow.

5. The device for relaxing the skin of the head according to claim 1, wherein said protuberances are solid.

6. The device for relaxing the skin of the head according to claim 1, wherein said elongate member is an elongate thin plate, said plurality of protuberances being provided at said predetermined interval on the inner side of said thin plate.

7. The device for relaxing the skin of the head according to claim 6, wherein said protuberances are hollow.

8. The device for relaxing the skin of the head according to claim 7, wherein said protuberances are solid.

9. A device for relaxing the skin of the head comprising an attachment member capable of being removably attached to the head and head skin push-up members each provided on each inner side of said attachment member said head skin push-up members each including an elongate member made of a soft material and having an enclosed space filled with a fluid such as a gas and a plurality of protuberances provided at a predetermined interval on the inner side of said elongate member.

10. The device for relaxing the skin of the head according to claim 9, wherein said protuberances are hollow.

11. The device for relaxing the skin of the head according to claim 9, wherein said protuberances are solid.

* * * * *